(12) United States Patent
Kuyava et al.

(10) Patent No.: US 7,344,554 B2
(45) Date of Patent: Mar. 18, 2008

(54) KEITH NEEDLE FOR FURLOW INSERTION TOOL

(75) Inventors: Charles C. Kuyava, Eden Prairie, MN (US); James Taylor, Lombard, IL (US)

(73) Assignee: AMS Research Corporation, Minnetonka, MN (US)

( * ) Notice: Subject to any disclaimer, the term of this patent is extended or adjusted under 35 U.S.C. 154(b) by 693 days.

(21) Appl. No.: 10/375,800

(22) Filed: Feb. 26, 2003

(65) Prior Publication Data

US 2004/0167574 A1 Aug. 26, 2004

(51) Int. Cl.
*A61B 17/06* (2006.01)
*A61F 5/00* (2006.01)

(52) U.S. Cl. .............. 606/224; 606/185; 606/225; 600/40; 66/116

(58) Field of Classification Search .............. 606/139, 606/144–150, 166, 181–183, 222–227, 188, 606/185, 116, 117, 44, 184; 604/272, 57, 604/59, 61, 273, 243, 27; 66/116–124; 600/40
See application file for complete search history.

(56) References Cited

U.S. PATENT DOCUMENTS

| | | | | |
|---|---|---|---|---|
| 4,133,339 A | * | 1/1979 | Naslund | 132/323 |
| 4,244,370 A | | 1/1981 | Furlow et al. | |
| 4,332,323 A | * | 6/1982 | Reenstierna | 206/365 |
| 4,508,119 A | * | 4/1985 | Tukamoto | 606/189 |
| 4,667,860 A | * | 5/1987 | Feuerman | 223/99 |
| 4,950,279 A | * | 8/1990 | Chang | 606/189 |
| 5,236,443 A | | 8/1993 | Sontag | |
| 5,250,054 A | * | 10/1993 | Li | 606/148 |
| 5,433,722 A | * | 7/1995 | Sharpe et al. | 606/148 |
| 5,433,728 A | | 7/1995 | Kim | |
| 5,676,675 A | | 10/1997 | Grice | |
| 5,683,416 A | | 11/1997 | McGregor et al. | |
| 5,693,071 A | | 12/1997 | Gorecki | |
| 5,693,072 A | | 12/1997 | McIntosh | |

(Continued)

*Primary Examiner*—Michael J. Hayes
*Assistant Examiner*—Michael G. Mendoza
(74) *Attorney, Agent, or Firm*—Kimberly K. Baxter

(57) ABSTRACT

The present disclosure is directed to a medical device or article that reduces the ability of the Keith needle to unintentionally fall out of the barrel, improves the ability of the Keith needle to track on axis, or both. In one aspect, the disclosure is directed toward a medical device suitable for use in implant surgery. The medical device includes a Furlow insertion tool with a barrel having a bore. The Furlow tool further includes an obturator adapted for slidable insertion into the bore. The medical device further includes a Keith needle adapted for slidable insertion into the bore. The Keith needle is adapted to yieldably fit against at least one of the barrel and the obturator when the Keith needle is disposed within the bore. In another aspect, the present disclosure is directed toward a Keith needle adapted for use with a Furlow insertion tool. The Furlow insertion tool including a barrel and an obturator. The barrel includes a bore having a diameter such that the Keith needle is adapted to be disposed within the bore. The Keith needle includes a blunt portion adapted to contact the obturator, a tip portion including a sharp end, and an interference portion operably coupled to the blunt portion and the tip portion. The interference portion has an operating thickness of at least the diameter of the bore to yeildably fit the Keith needle against the barrel when the Keith needle is disposed within the bore.

30 Claims, 4 Drawing Sheets

U.S. PATENT DOCUMENTS

| | | | |
|---|---|---|---|
| 5,868,729 A * | 2/1999 | Pelfrey | 606/1 |
| 5,891,164 A | 4/1999 | Dabir | |
| 5,897,572 A | 4/1999 | Schulsinger et al. | |
| 5,902,320 A | 5/1999 | Matsutani et al. | |
| 5,913,875 A | 6/1999 | Smith et al. | |
| 5,993,408 A | 11/1999 | Zaleski | |
| 6,129,741 A | 10/2000 | Wurster et al. | |
| 6,159,233 A | 12/2000 | Matsuzawa | |
| 6,322,581 B1 | 11/2001 | Fukuda et al. | |
| 6,514,263 B1 | 2/2003 | Stefanchik et al. | |
| 6,551,339 B2 * | 4/2003 | Gavronsky | 606/189 |

* cited by examiner

KEITH NEEDLE FOR FURLOW INSERTION TOOL

BACKGROUND

The present disclosure relates to medical devices used in implant surgery. More specifically, the present disclosure relates to a Furlow insertion tool and Keith needle.

The study of impotence has recently become center stage in the field of medicine. In the early 1970's, the conventional view was that ninety percent of impotence cases were psychologically based, whereas only ten percent of the cases were caused by a physical condition. Today, doctors and scientists understand that the overwhelming majority of cases are caused by a physical condition. Accordingly, more and more resources are poured into the study of and treatment for impotence. In a recent study, fifty-two percent of men between the ages of forty and seventy self-reported that they suffer from some type of erectile dysfunction. Another study estimated that over thirty million American men and their partners suffer from erectile dysfunction.

Advertisements for pharmaceutical treatments for impotence have become ubiquitous, and include endorsements from celebrities that suffer from erectile dysfunction. More and more men and their partners now are seeking treatment for impotence. In the recent past, it was estimated that only one in twenty suffers of erectile dysfunction sought treatment from their doctors. Pharmaceutical treatments are successful for only a subset of impotence sufferers. More invasive treatments are necessary for many men. These treatments include injection therapy, vacuum devices and penile prosthesis.

For many impotence sufferers, the penile prosthesis, or penile implant, is the only solution to restore a happy and healthy sex life. The penile implant has been used for decades and provides a selected and reliable erection. The penile implant often includes a pair of cylinders. In some instances, these cylinders are inflatable, which are connected to a fluid-filled reservoir with a pump and valve assembly. The two cylinders are normally implanted into the corpus cavernosae of the patient's penis and the reservoir is typically implanted into the patient's abdomen. The pump assembly is implanted in the scrotum. During use, the patient actuates the pump and fluid is transferred from the reservoir through the pump and into the cylinders. This results in the inflation of the cylinders and produces rigidity for a normal erection. Then, when the patient desires to deflate the cylinders, a valve assembly within the pump is actuated in a manner such that the fluid in the cylinders is released back into the reservoir. This deflation returns the penis to a flaccid state.

The penile implant is an invasive treatment and requires a delicate and painful implant surgery to install. To reach the corpus cavernosum and implant the cylinders, the surgeon will first make an incision at the base of the penis, such as where it meets the scrotum. The patient is prepared for the cylinder after the surgeon has dilated each corpus cavernosum to create space for the cylinders.

Once the patient has been prepared, the surgeon will insert a medical device known as a Furlow insertion tool with a Keith needle into the dilated corpus cavernosum. The Furlow tool is a well known and often used device in the art and is described in U.S. Pat. No. 4,244,370, which was filed in 1978. The Furlow tool is a long slender device having a hollow barrel with a plunger device known as an obturator at the rearward end. The Keith needle is also a well-known article used in many areas of medicine that looks much like a heavy straight sewing needle, but is used instead to pierce tissue. The Keith needle fits within the barrel and is ejected from the forward end with the obturator.

In order to install the implant, the Keith needle is attached to a suture that is also attached to the cylinder. The Furlow tool is advanced into the corpus cavernosum until the forward end is inside of the crown of the penis, or glans. At this point, the cylinder and part of the suture attached to the cylinder remain outside of the patient's body. The Furlow tool is used to force the Keith needle out of the barrel and through the glans. The surgeon grasps the Keith needle from outside of the body and pulls it from the penis leaving the suture threaded through the corpus cavernosum. The Furlow tool is withdrawn from the penis. The suture is then pulled to draw the cylinder into the incision and the corpus cavernosum. Once the implant is in place, the suture is removed. This procedure is performed for each corpus cavernosum. The incision at the base of the penis is closed and the hole in the glans from the Keith needle is permitted to heal closed. The recovery process can be several weeks to a few months.

As mentioned, Keith needles are used in many areas of medicine. One such use has been to puncture a patient's chest to adjust pacemaker settings. The Keith needle often used in penile implant surgery is often an abdominal Keith needle and includes a triangular cross section and an eye. The cross sectional width of the Keith needle is less than the diameter of the bore in the hollow barrel of the Furlow tool. One reason is that the bore must also accommodate the suture extending through the eye of the needle. A narrow Keith needle is preferred to reduce trauma as it pierces the penis.

A surgeon typically encounters several issues when inserting the Furlow tool and ejecting the Keith needle. One issue with this configuration is that the Keith needle could fall out of the barrel under the force of gravity. If the medical personnel are not careful, the Keith needle could fall out and they could pierce themselves, the patient, or the inflatable cylinder, which could damage or ruin the cylinder. This problem is prevalent and many medical professionals have now adopted a specialized grip on the suture and the barrel when handling the Furlow tool. This grip, in addition to being uncomfortable, often leads to the medical professional's surgical gloves being pinched or caught in the Furlow tool.

Another issue often encountered by the surgeon relates to the fact that the Keith needle can rest "off-axis" inside the wider barrel of the Furlow tool. If the needle exits the Furlow tool at an angle, it can track incorrectly through the penis and exit the glans at an unintended or undesired location. This may require the surgeon to re-pierce the penis, causing further trauma.

SUMMARY

The present disclosure is directed to a medical device or article that reduces the ability of the Keith needle to unintentionally fall out of the barrel, improves the ability of the Keith needle to track on axis, or both. Surgeons and other medical professionals are able to use an intended and comfortable grip when handling the Furlow tool, and the device will not appreciably increase the trauma to the penis, if at all.

In one aspect, the disclosure is directed toward a medical device suitable for use in implant surgery. The medical device includes a Furlow insertion tool with a barrel having a bore. The Furlow tool further includes an obturator adapted for slidable insertion into the bore. The medical device, further includes a Keith needle adapted for slidable insertion into the bore. The Keith needle is adapted to yieldably fit against at least one of the barrel or the obturator when the Keith needle is disposed within the bore.

In another aspect, the present disclosure is directed toward a Keith needle adapted for use with a Furlow insertion tool. The Furlow insertion tool includes a barrel and an obturator. The barrel includes a bore having a diameter such that the Keith needle is adapted to be disposed within the bore. The Keith needle includes a blunt portion adapted to contact the obturator, a tip portion including a sharp end, and an interference portion operably coupled to the blunt portion and the tip portion. The interference portion has an operating thickness of at least the diameter of the bore to yeildably fit the Keith needle against the barrel when the Keith needle is disposed within the bore.

In still another aspect, the present disclosure is directed towards a Keith needle adapted for use with a Furlow insertion tool. The Furlow insertion tool includes a barrel having a bore extending through the barrel, wherein the bore includes a diameter. The Keith needle includes a blunt end, a sharp end generally opposite the Keith needle from the blunt end, and a spring disposed between the blunt end and the sharp end. The spring includes an operating thickness at least the diameter of the bore. The Keith needle is adapted to be disposed within the bore such that the spring is urged against the barrel.

In still another aspect, the present disclosure is directed to an article adapted for use with a Furlow insertion tool. The Furlow insertion tool includes a barrel having a bore where the bore includes a diameter. The article includes a longitudinally extending needle having a blunt end and an opposite sharp end. The needle includes a cross section having a width, where the width of the cross section is less then the diameter of the bore. The needle includes a plurality of bends such that the needle provides an operating thickness that is at least the diameter of the bore.

DESCRIPTION

This disclosure relates to medical devices and articles used in surgery. Specifically, the disclosure, including the figures, describes a Keith needle and Furlow insertion tool with reference to a several illustrative examples. Other examples are contemplated and are mentioned below or are otherwise imaginable to someone skilled in the art. The scope of the invention is not limited to the few examples, i.e., the described embodiments of the invention. Rather, the scope of the invention is defined by reference to the appended claims. Changes can be made to the examples, including alternative designs not disclosed, and still be within the scope of the claims.

Figure 1:
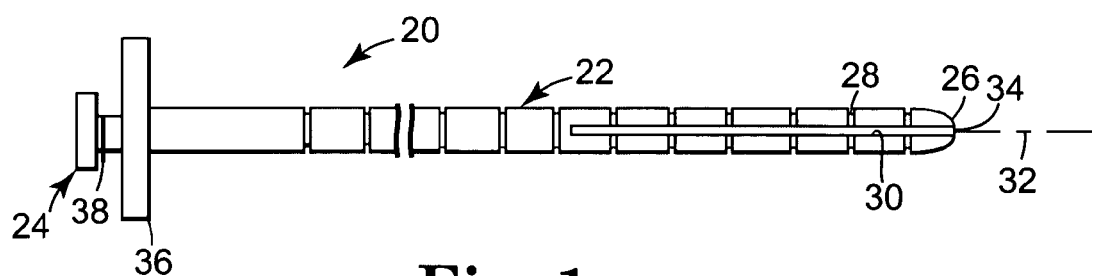
FIG. 1 is a side view of a Furlow tool and Keith needle adapted to implant medical prosthesis devices.

FIG. 1 shows a medical device including a Furlow insertion tool and a Keith needle. Furlow insertion tool 20 having a barrel 22 and an obturator 24 slidably inserted into the barrel 22. A Keith needle is also slidably inserted into the barrel 22, but is not visible in the figure.

Figure 2:
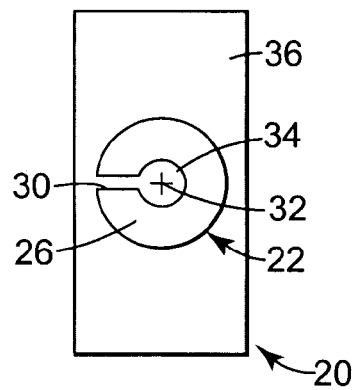
FIG. 2 is a front view of the Furlow tool and Keith needle of FIG. 1.

The barrel 22 includes a rounded forward end 26 that is adapted to allow insertion into a body cavity. Markings 28 are applied to the outer surface of the barrel 22 and allow a medical professional to determine the depth that the barrel 22 has been inserted into the body cavity. In one example, the markings 28 are circumferential grooves in the barrel 22 that are spaced apart at one-centimeter intervals. A barrel slot 30 is included in the barrel 22, proximate the forward end 26, that is generally parallel to an axis 32 of the barrel 22. FIG. 2 shows the slot 30 is in communication with a bore 34 extending along the axis 32 of the barrel. The bore 34 includes a diameter. Referring back to FIG. 1, a handle 36 is included with the barrel 22 opposite the forward end 26. In the example, the handle 36 includes a detent mechanism, such as a spring 38 or plunger, that is yieldably urged against the obturator 24.

Figure 3:
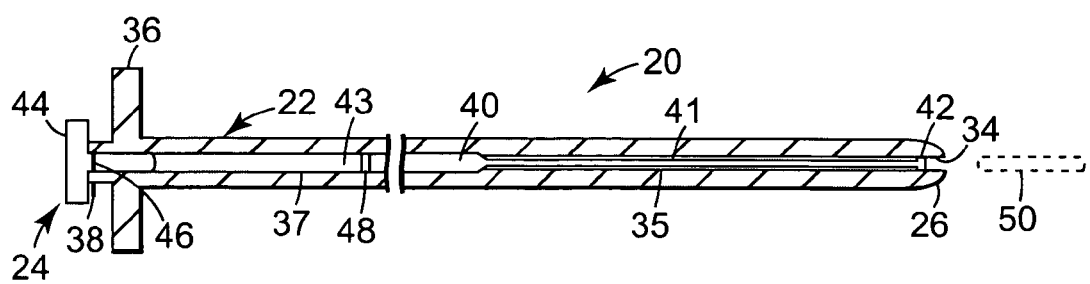
FIG. 3 is a side sectional view of the Furlow tool of FIG. 1.

The obturator 24 is described with reference to FIG. 3. The obturator 24 is slidably inserted into the bore 34. The obturator 24 includes a shaft 40 having a forward end 42 and a handle 44 attached to the end opposite the forward end 42. The obturator 24 is slidably pulled out of the barrel 22 by grasping the handle 44 and pulling away from the barrel handle 36. Similarly, a Keith needle 50 (shown schematically and in phantom) is forced out of the forward end 26 of the barrel 22 by pushing the handle 44 toward the barrel handle 36.

The shaft 40 can include an extension groove 46 and a retraction groove 48. Grooves 46, 48 are circumferential grooves spaced-apart at predetermined positions along the shaft 40. Cooperation between the grooves 46, 48 and the detent mechanism, shown as spring 38, provides stable positions of the obturator 24 relative to the barrel 22. For example, the obturator is in a retracted position when the detent mechanism is yieldably urged against groove 48. The obturator is in an extended position when the detent mechanism is yieldably urged against groove 46, as shown in the figure.

The Keith needle 50 is disposed inside the barrel 22 when the obturator is in the retracted position. In the example, the entire Keith needle 50 is within the barrel 22 and the tip of the needle 50 does not extend past the forward end 26. As the handle 44 is urged toward the barrel handle 36, the Keith needle 50 is pushed from the barrel 22 at the forward end 26 until the Keith needle 50 is ejected from the Furlow tool 20.

The shaft 40, in some examples, includes a forward shaft segment 41 and a rearward shaft segment 43. The forward shaft segment 41 fits closely within the forward bore 35. The rearward shaft 43, in the example, is larger in diameter than the forward shaft 41, and the rearward shaft 43 remains strong and rigid when grooves 46, 48 are included in the obturator 24. The rearward shaft 43 fits within a rearward bore 37, and the rearward bore 37 is larger in diameter than the forward bore 35. Other configurations are possible. In this example, the Furlow tool 20 receives the Keith needle 50 entirely within the forward bore 35, i.e., the Keith needle 50 does not extend into the rearward bore 37. If an example is provided where the Keith needle is adapted to fit entirely within a bore having more than one diameter, the term diameter of the bore is understood to mean the smallest diameter.

Figure 4:
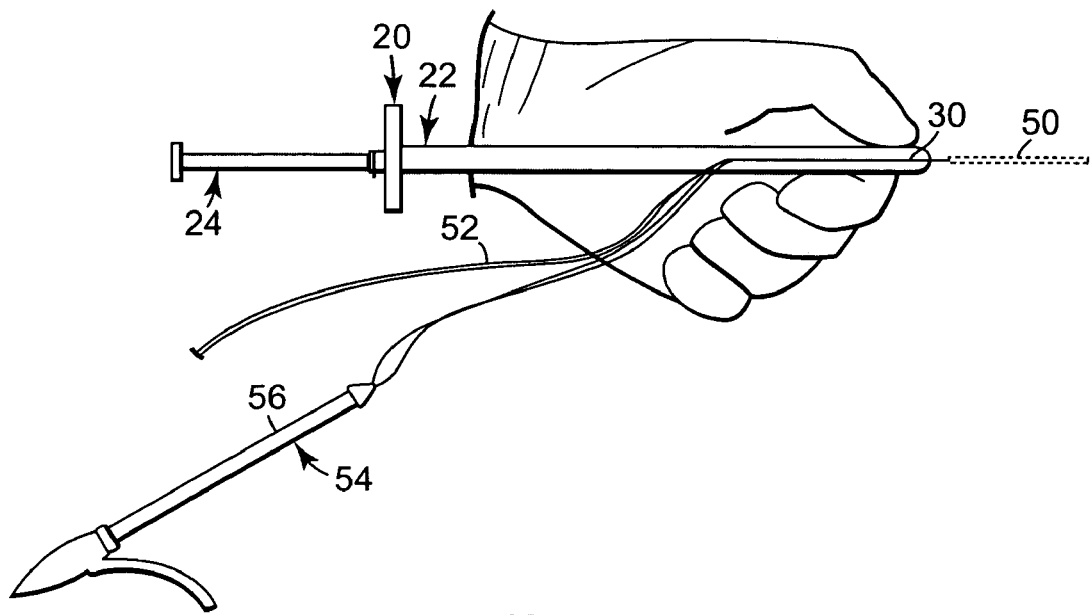
FIG. 4 illustrates use of the Furlow tool and Keith needle of FIG. 1 where a suture strand is attached to the Keith needle and to a prosthesis in preparation for implant surgery.

FIG. 4 shows a Furlow tool 20 in the retracted position. The Keith needle is slidably inserted into the barrel 22 and extends longitudinally along the axis 32. A traction suture 52 is attached to the Keith needle 50. In the example, the suture 52 is threaded through the eye of the needle 50. The suture 52 extends through the barrel slot 30 and is also connected to an implant 54 such as an inflatable penile prosthesis, or cylinder 56 as shown in the figure. The figure shows a surgical professional holding only the barrel 22. The Keith needle 50 is adapted to fit within the barrel 22 such that the Keith needle 50 will not drop out of the bore 34 through the forward end 24 under the force of gravity.

In the case of penile prosthesis surgery, the surgeon will dilate the patient's corpus cavernosum to prepare the patient to receive the cylinder 56. The corpus cavernosum is one of two parallel columns of erectile tissue forming the dorsal part of the body of the penis, i.e., two slender columns that extend substantially the length of the penis. To reach the corpus cavernosum, the surgeon will first make an incision such as a penoscrotal incision made on the underside of the penis where it meets the scrotum. The patient is prepared for the cylinder 56 after the surgeon has dilated the corpus cavernosum to create space for the cylinder 56, and has measured the corpus cavernosum to help select the appropriate cylinder 56. The corpus cavernosum can be measured with the markings 28 on the barrel 22. In a typical surgery, each corpus cavernosum is prepared to receive a cylinder 56.

Figure 5:
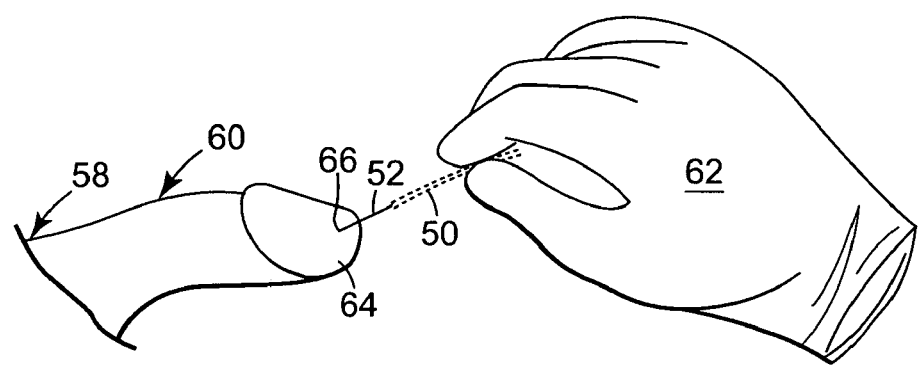
FIG. 5 illustrates a procedure of the implant surgery.

Once the patient is prepared, the surgeon will insert the Furlow tool 20 and Keith needle 50 into the dilated corpus cavernosum. In the example, the barrel 22 including the Keith needle 50 with the attached suture 52 is inserted into the penoscrotal incision. The barrel is advanced into the corpus cavernosum until the rounded forward end is inside of the crown of the penis, or the glans. The cylinder 56 and part of the suture 52 attached to the cylinder remain outside of the patient's body. The obturator handle 44 is then advanced toward the barrel handle 36 until the obturator 24 has reached the forward or extended position. As illustrated in FIG. 5, the Keith needle 50 is thus forced out of the barrel 22 and through the glans 64 at a point of exit 66. The surgeon 62 grasps the Keith needle 50 or part of the attached suture 52 (typically with a hemostat) from outside of the body 58 and pulls them from the penis 60 leaving the suture 52 threaded through the corpus cavernosum. The barrel 22 is withdrawn from the penis 60. The suture 52 is then pulled to draw the cylinder 56 into the incision and the corpus cavernosum. Once the implant is in place, the suture 52 is removed.

Figure 6:
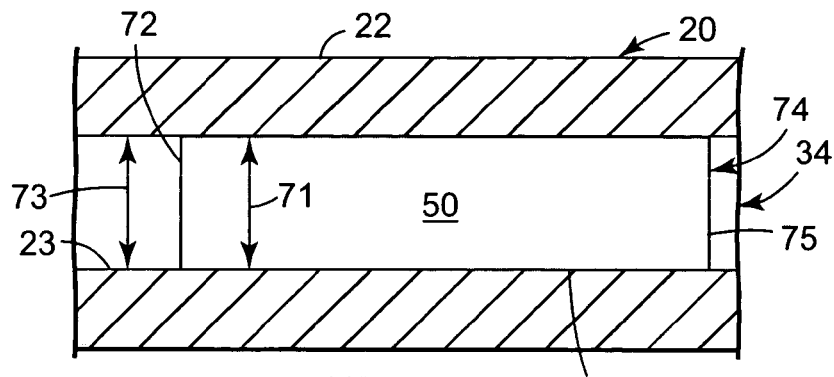
FIG. 6 is a block diagram of the Furlow tool and the Keith needle of FIG. 1.

FIG. 6 shows a schematic diagram of the Keith needle 50 disposed within the Furlow insertion tool 20. The Keith needle 50 is disposed within the barrel 22, and the obturator 24 is in the retracted position. In the related art, the Keith needle was a straight abdominal needle that could fall out of a barrel under the force of gravity. In the present disclosure, however, the Keith needle 50 is yeildably fit within the Furlow tool 22. Specifically, the Keith needle is slidably inserted into the bore 34, and the Keith needle is adapted to be yeildably fit against at least one of the barrel or the obturator when the Keith needle is disposed within the bore. In order to insert the Keith needle when it yeildably fits against the barrel, the handler of the medical device will typically pull back on the suture until the needle is in place within the barrel. One example of a Keith needle adapted to be yeildably fit against the barrel and the obturator is to magnetize a straight abdominal Keith needle. In this case, the magnet force will urge the Keith needle against the side of the bore and the tip of the obturator 24. The magnetic force is sufficiently strong enough to prevent the Keith needle from moving in the direction of the axis under the force of gravity. In a variation of this example, either the barrel or the obturator is magnetized instead of the Keith needle. One skilled in the art can now imagine other combinations of magnetized parts of the medical device.

In another example, the Keith needle 50 of FIG. 6 includes an interference portion 70 that has an operating thickness 71 of at least the diameter 73 of the bore 34 to yeildably fit the needle 50 against the barrel 22 when the needle is disposed within the bore 34. In the example, the needle is yeildably fit against the inside wall 23 of the barrel 22. In other words, the interference portion 70 provides an interference fit with the inside of the barrel 22. The force against the inside of the barrel 22 is sufficient to overcome the force of gravity and will prevent the needle 50 from falling out of the forward end 26. The force of the interference fit, however, is not so great as to prevent a handler from ejecting the needle 50 from the barrel 22 with the obturator 24.

The needle 50 also includes a blunt portion 72 and a tip portion 74 operably coupled to the interference portion 70. The blunt portion is adapted to contact the obturator 24. In one example, the needle 50 is placed within the barrel 22 blunt portion 72 first. The obturator 24 presses against the blunt portion 72 as the obturator 24 is forced from the retracted to the extended position relative to the barrel 22. The tip portion 74 includes a sharp end 75 that, in the example, is adapted to pierce tissue. In the example, the tip portion 74 exits the front end 26 first when the obturator 24 forces the needle 50 from the barrel 22.

An example of the Keith needle 50 yeildably fit against the inside wall 23 of the barrel with an interference portion 70 is a needle that is as wide as the bore 34. Specifically, the needle can be manufactured to be thick and fit within the bore of typical Furlow tools. Also, a Furlow tool can be manufactured so as the bore is about the size of a standard abdominal Keith needle.

Figure 7:
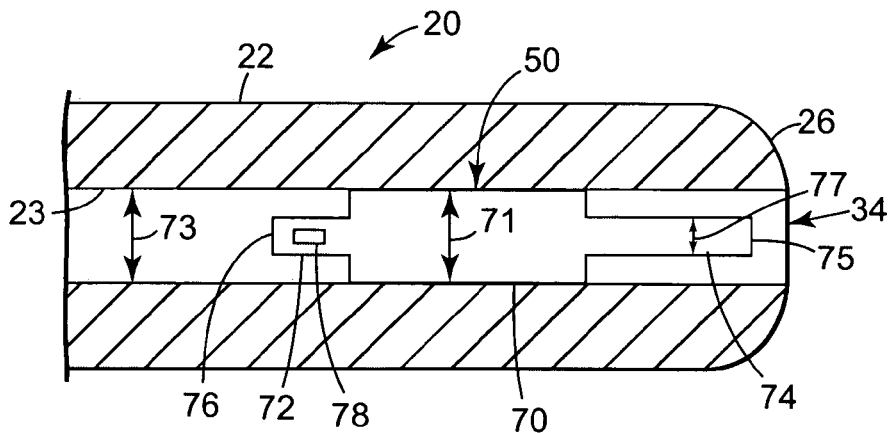
FIG. 7 is a block diagram of an example of the Keith needle of FIG. 5.

FIG. 7 shows one example of the Keith needle 50 of FIG. 6. The blunt portion includes a blunt end 76 and can include an attachment article 78. The blunt end 76 is adapted to directly contact the obturator 24. For example, the obturator 24 presses against the blunt end 76 when the needle 50 is forced from the barrel 22. The attachment article 78 is the part of the needle 50 that is adapted to attach to the suture 52, such as an eye. In other examples, the attachment article need not be included with the blunt portion, and can be included with another portion.

The blunt portion 72 and the tip portion 74 include a cross section having a width 77. In many examples, the width of the cross section of the blunt portion is the same as the width of the cross section of the tip portion, although this need not be the case. When the term width is used to without reference to either the blunt portion or the tip portion, width is used to describe the largest cross section of the needle. The width of the blunt portion 72 and tip portion 74 cross sections are chosen to provide strength and rigidity to the needle. Another factor in the width is to minimize the necessary trauma to the tissue that the needle passes through. Accordingly, the width of the cross section is chosen to be rather small while still imparting strength and rigidity. The width of the tip portion and the blunt portion is typically less than the smallest diameter of the bore.

The width of the needle in the example of FIG. 6 is shown to be the same as the diameter of the bore 73 and the operating thickness 71 of the interference portion 70. The width of the tip 74 and blunt portions 72 of the needle in FIG. 7 is shown to be less than the diameter 73 of the bore and less than the operating thickness 71. The operating thickness 71 of the interference portion includes the thickness of the interference portion as it interacts with the inside wall 23 of the barrel 22. In other words, the operating thickness is the thickness of the needle measured in a direction generally perpendicular to the direction of the sharp end (or the axis when the needle is disposed within the bore). In one example, the interference portion of the needle includes a cross-sectional width 77 that is at least as large as the diameter 73 of the bore. In another example, a Keith needle having a width 77 less than the diameter of the bore 73 is configured in such a way at the interference portion so as to yeildably fit within the bore. Examples of this are shown in FIGS. 8 and 9, described in more detail below.

Figure 8A:
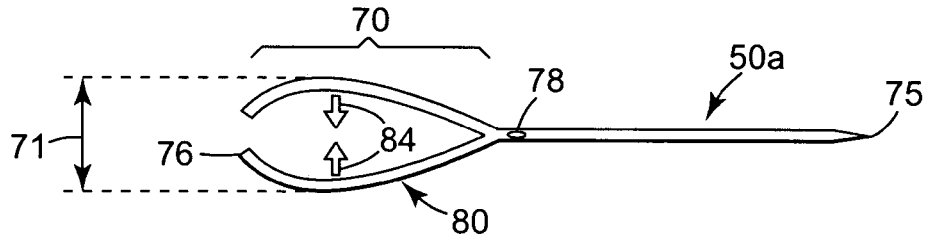
FIGS. 8a and 8b are side views of one example of a Keith needle adapted for use with the Furlow tool of FIG. 1.
Figure 8B:
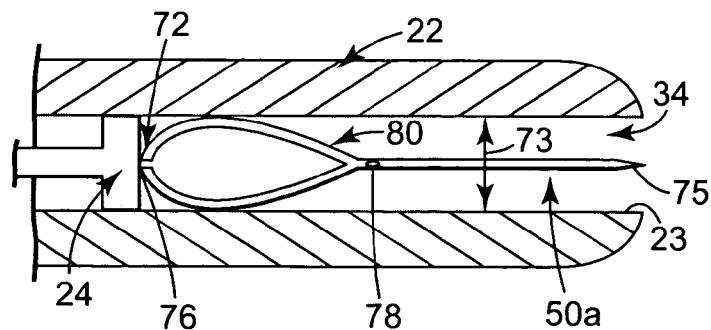
Figure 9:
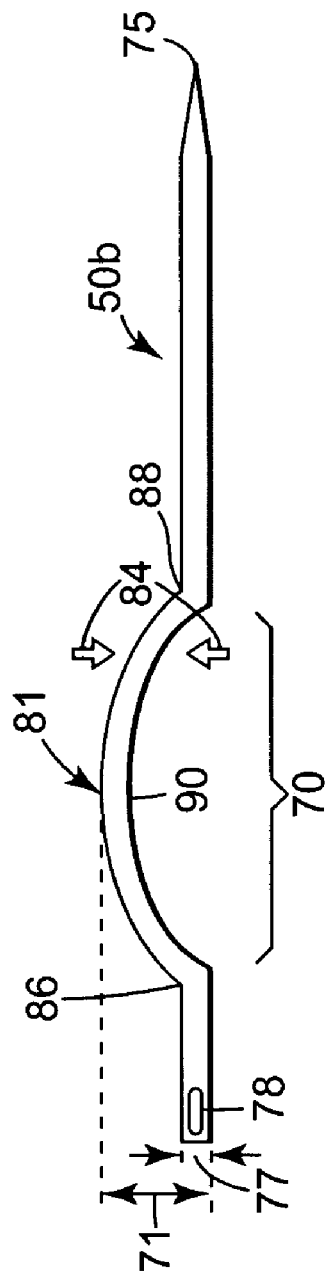
FIG. 9 is a side view of another example of a Keith needle adapted for use with the Furlow tool of FIG. 1.
Figure 10:
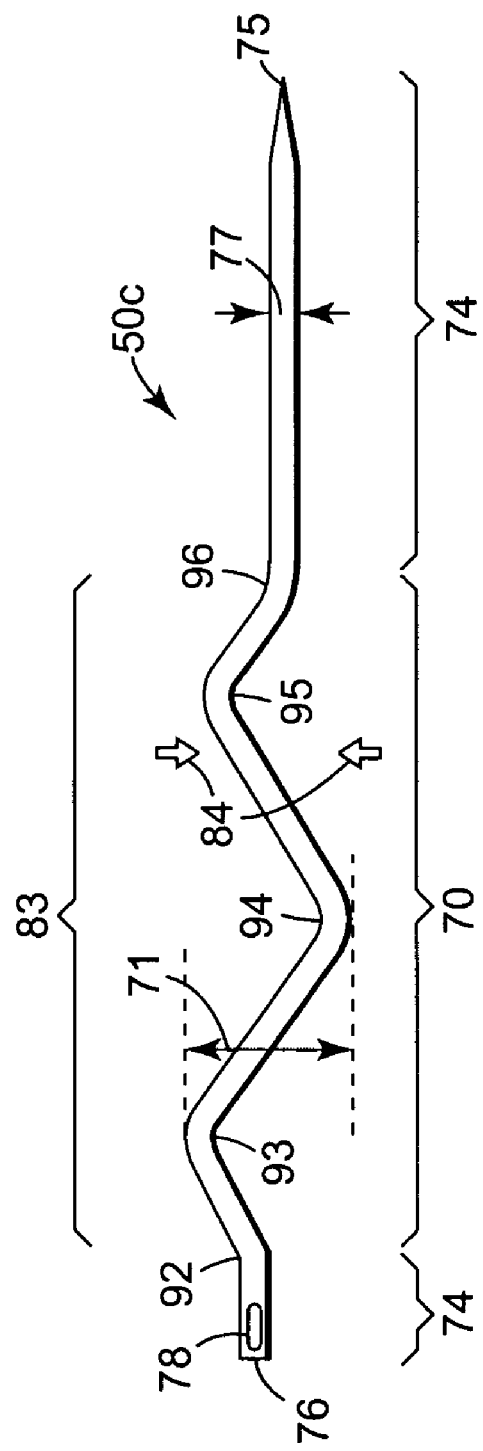
FIG. 10 is a side view of another example of a Keith needle adapted for use with the Furlow tool of FIG. 1.

FIGS. 8 through 10 show examples where the interference portion of the needle is configured to be a spring disposed between the blunt end and the sharp end. The spring, which corresponds with the interference portion shown in FIG. 7, includes an operating thickness of at least the diameter of the bore. In the examples, the springs are urged against the inner wall of the barrel to provide a force component in a direction perpendicular to the axis of the bore.

Accordingly, the spring force is in a direction perpendicular to the axis to yeildably fit the needle against the barrel to prevent unintentional movement of the needle along the axis.

FIG. 8a and 8b show a side view of a first example of a needle 50a where the interference portion 70 includes a spring 80. In this example, the spring is a leaf spring. The spring 80 is deflectable a direction generally perpendicular to the direction of the sharp end, or along the diameter of the bore. In this example, the needle 50a has an operating thickness 71 that is greater than the diameter 73 of the bore when the needle 50a is not disposed within the bore, as shown in FIG. 8a. The spring 80 is deflected in the direction of the arrows 84 in order for the needle to fit within the bore 34. The spring is urged against the inside wall 23 of the barrel 22 when the needle 50a is disposed within the bore 34, as shown in FIG. 8b. The spring 80 comes together to form a blunt portion or specifically a blunt end 76.

FIGS. 9 and 10 also show side view of examples of needles 50b, 50c respectively, having a spring 81, 83 respectively, disposed between the blunt end and the sharp end, where the spring has an operating thickness of at least the diameter of the bore. The springs 81, 83 also deflect in the direction of arrows 84 if the operating thickness 71 is greater than the diameter 73 of the bore. In addition, FIGS. 9 and 10 show two of many examples of needles configured in such a way that the operating thicknesses 71 are greater than the cross sectional widths 77 of the needles. Specifically, the figures show needles 50b, 50c with a plurality of bends that provide the operating thickness 71.

In FIG. 9, the needle 50b includes three bends 86, 88, 90. A typical abdominal Keith needle is bent at three locations to provide an interference portion 70 that will yeildably fit against the inner wall 23 of the barrel. In one example, the operating thickness 71 is either the diameter 73 of the bore or just slightly larger than the diameter of the bore so that the generally rigid spring 81 will not deflect a substantial amount. The bends need not be abrupt, but can be a gradual deviation from the straight. Further, the location of the bend need not be clearly defined, but can encompass a region of the needle, such as bend 90.

FIG. 10 shows a needle 50c including five bends 92, 93, 94, 95, 96. The tip portion 74 includes a triangular cross section that blends into a generally oval or round cross section at the interference portion 70. The blunt portion 72 includes a thin oval cross section and an eye 78 is included proximate the blunt end 76. The five-bend construction has advantages over straight Keith needles of the prior art in that the needle of FIG. 10 has been demonstrated to exit the barrel generally along the axis 32, and remains on axis longer than needles of the prior art.

In addition, the five-bend construction has been demonstrated to have an "effective width" that is generally the same as a straight needle. "Effective width" means the width of the needle as it interacts with the pierced tissue. The five-bend construction creates a hole in the tissue that is generally as wide as the width 77 of the cross section of the needle. This can be more advantageous than creating a larger hole, say on the size of the operating thickness 71. A smaller effective width requires less force to pass the needle through the tissue, tracks through the tissue more accurately, and causes less trauma to the tissue than a wider effective width.

Bends in the needle can take a variety of configurations. For example, a bend can be abrupt and give the needle a "saw-tooth" configuration, a bend can be gradual and give the needle a sinusoidal wave configuration, or the like. More bends in the needle aid in tracking but decrease compressibility in the direction perpendicular to the axis. The five bend configuration has been demonstrated to provide an optimized amount of compressibility and tracking.

The present invention has now been described with reference to several embodiments. The foregoing detailed description and examples have been given for clarity of understanding only. Those skilled in the art will recognize that many changes can be made in the described embodiments without departing from the scope and spirit of the invention. Thus, the scope of the present invention should not be limited to the exact details and structures described herein, but rather by the appended claims and equivalents.

What is claimed is:

1. A medical device suitable for use in implant surgery, the medical device, comprising:
   a Furlow insertion tool including a barrel having a bore, the Furlow insertion tool further comprising an obturator adapted for slidable insertion into the bore; and
   a Keith needle adapted for slidable insertion into the bore;
   wherein the Keith needle is adapted to yieldably fit against at least one of the barrel and the obturator when the Keith needle is disposed within the bore, the bore includes a diameter, and the Keith needle includes an interference portion having an operating thickness that is at least the diameter.

2. The medical device of claim 1, wherein the Keith needle is magnetized.

3. The medical device of claim 2, wherein the Keith needle, includes a width that is less than the diameter of the bore.

4. The medical device of claim 1, wherein the Keith needle further includes a blunt portion and a tip portion, each operably coupled to the interference portion.

5. A Keith needle and a Furlow insertion tool combination, comprising:
   a Furlow insertion tool comprising an elongated barrel including a barrel bore having a diameter and an elongated obturator adapted to be inserted into at least a portion of the barrel bore; and a Keith needle having a blunt portion adapted to contact the obturator when the Keith needle is inserted within a portion of the barrel bore, a tip portion including a sharp end, and an interference portion operably coupled to the blunt portion and the tip portion, the interference portion having an operating thickness of at least the diameter of the bore to yieldably fit the Keith needle against the barrel when the Keith needle is disposed within the bore.

6. The Keith needle and Furlow insertion tool of claim 5, wherein the Keith needle includes an eye adapted to receive a suture.

7. The Keith needle and Furlow insertion tool of claim 6, wherein the eye is proximate the blunt portion.

8. The Keith needle and Furlow insertion tool of claim 5, wherein the interference portion is urged against the barrel.

9. The Keith needle and Furlow insertion tool of claim 8, wherein the interference portion includes a spring mechanism urged against the barrel.

10. The Keith needle and Furlow insertion tool of claim 9, wherein the spring mechanism includes an operating thickness greater than the diameter of the bore.

11. A Keith needle adapted for use with a Furlow insertion tool to deliver the Keith needle at a tissue site and pass the needle into tissue, the combination of Keith needle and Furlow insertion tool comprising:

a Keith needle; and a Furlow insertion tool comprising an elongated barrel including a bore having a diameter in which the Keith needle is disposable and an obturator adapted to eject the Keith needle from the bore;

wherein Keith needle includes an elongated needle shaft having a diameter less than the barrel bare diameter and extending between a needle blunt end, and a needle sharp end, at least a section of the needle shaft shaped as a spring disposed between the blunt end and the sharp end, the spring extending at least a portion of the needle shaft into contact with the bore, whereby the Keith needle is adapted to be disposed within the bore such that a spring force urges at least a portion of the needle shaft against the barrel to retain the Keith needle within the bore and enable slidable movement of the Keith needle along the bore.

12. The needle and tool combination of claim 11, wherein the spring is deflectable in a direction of the diameter of the bore.

13. The needle and tool combination of claim 12, wherein the spring is deflectable to form the blunt end when disposed within the bore.

14. The needle and tool combination of claim 11, wherein the spring is formed with a plurality of bends in the Keith needle shaft.

15. The needle and tool combination of claim 11, wherein the spring is a leaf spring.

16. A needle insertion system for use in surgery to pass a needle through tissue, the system comprising:

a needle insertion tool comprising an elongated barrel having a barrel bore, wherein the bore includes a diameter;

a surgical needle longitudinally extending between a needle blunt end and a needle sharp end, the needle having a cross-section having a width, wherein the width of the cross-section is less than the diameter of the bore and the needle includes a plurality of bends such that the needle provides an operating thickness that is at least the diameter of the bore, and wherein the effective width of the needle at the plurality of bends is substantially similar to the effective width of the needle at the blunt end; and a needle ejection tool adapted to be extended into the barrel bore to slidably move the surgical needle along and out of the barrel bore.

17. The article of claim 16, wherein the plurality of bends includes three or more bends.

18. The article of claim 17, wherein the plurality of bends is five bends.

19. A needle insertion system for use in surgery to pass a needle through tissue, the system comprising:

a needle insertion tool comprising an elongated barrel that is formed at least in part of a magnetized or magnetically attractable material and encloses a barrel bore having a bore cross-section dimension;

a surgical needle longitudinally extending between a needle blunt end and a needle sharp end, the needle having a cross-section dimension less than the bore cross-section dimension whereby the needle is insertable into the barrel bore, wherein at least a portion of the needle is formed of a material providing a magnetic force of attraction with the barrel; and a needle ejection tool adapted to be extended into the barrel bore to overcome the magnetic force of attraction and slidably move the surgical needle along and out of the barrel bore.

20. A needle insertion system for use in surgery to pass a needle through tissue, the system comprising:

a needle insertion tool comprising an elongated barrel that encloses a barrel bore having a bore cross-section dimension bounded by a bore side;

a surgical needle longitudinally extending between a needle blunt end and a needle sharp end, the needle having a cross-section dimension less than the bore cross-section dimension whereby the needle is insertable into the barrel bore, the surgical needle further comprising means for yieldably applying at least a portion of the surgical needle against the bore side to retain the surgical needle within the bore; and means for applying force against the needle blunt end to move the surgical needle along and out of the barrel bore to pass the needle sharp end into tissue.

21. The needle insertion system of claim 20, wherein the applying substantially axially aligns the surgical needle along an axis of the bore as the surgical needle exits the bore.

22. A kit for passage of a suture through body tissue between a body cavity and the patient's skin comprising:

an insertion tool adapted to be passed into a body cavity, the insertion tool comprising an elongated barrel extending between a barrel forward end and a tool handle and having a barrel bore bounded by a bore side and extending from bore openings at the barrel forward end and tool handle, the barrel bore having at least one barrel bore dimension;

an elongated obturator having an elongated obturator shaft extending between a shaft forward end and an obturator shaft handle, the obturator shaft adapted to be inserted through the bore opening at the tool handle and into the bore to selectively dispose the obturator shaft forward end along the length of the barrel bore;

a needle having a needle shaft and needle shaft axis extending from a needle shaft tissue penetrating end and a needle shalt blunt end, the needle shaft having a needle shaft axis extending between the tissue penetrating end and the blunt end and a shaft dimension selected with respect to the barrel bore dimension to enable insertion of the needle into at least a distal portion of the barrel bore with the tissue penetrating end disposed toward the bore opening at the barrel forward end; and means for applying at least portions of the needle shaft against the bore side to retain the needle within the distal portion of the barrel bore while enabling slidable advancement and ejection of the needle out of the barrel bore and through tissue adjacent the barrel forward end upon advancement of the obturator shaft forward end within the barrel bore into engagement against the needle shaft blunt end and toward the barrel forward end.

23. The kit of claim 22, further comprising:
a length of suture attached to the needle shaft; and
a slot through the bore side in communication with the barrel bore along at least the distal portion of the barrel bore through which suture is extendable during advancement and ejection of the needle from the bore.

24. The kit of claim 22, wherein the applying means comprises a magnetic force3 of attraction of the needle against the barrel side effected by making at least a pardon of one or both of the needle and the barrel shaft of magnetized materials or mutually magnetically attractable materials.

25. The kit of claim 22, wherein:
the needle shaft has a needle shaft axis extending between the tissue penetrating the end and the blunt end; and
the applying means comprises means for exerting a spring force laterally of the needle shaft axis between the needle shaft and bore side.

26. The kit of claim 22, wherein:
the needle shaft has a needle shaft axis extending between the tissue penetrating end and the needle blunt end; and
the applying means comprises one or more bend in the needle shaft away from and back toward the needle axis effecting contact of at least one section of the needle shaft against the bore side and exerting a spring force laterally of the needle shaft axis between the needle shaft and bore side.

27. The kit of claim 26, wherein the applying means comprises a plurality of bends in the needle shaft away from and back toward the needle axis effecting a plurality of contacts of spaced apart sections of the needle shaft against the bore side.

28. The kit of claim 22, wherein:
the needle shaft has a needle shaft axis extending between the tissue penetrating end and the needle blunt end; and
the applying means comprises a pair of needle shaft bifurcations extending from bifurcation free ends at the needle shall blunt end to a point of mutual joinder intermediate the needle shaft blunt end and the needle shaft tissue penetrating end, at least one of the bifurcations extending away from and back toward the needle axis effecting contact of at least one section of the bifurcation against the bore side and exerting a spring force laterally of the needle shaft axis between the needle shaft and bore side.

29. The kit of claim 28, wherein both of the bifurcations extend away from and back toward the needle axis effecting contact of at least one section of each of the bifurcations against a surface of the bore side and exerting a spring force laterally of the needle shaft axis between the needle shaft and bore side.

30. The kit of claim 28, wherein the applying means further comprises means for exerting a plurality of offsetting spring forces laterally of the needle shaft axis between the needle shaft and bore side to substantially align the shall axis with the bore axis.

* * * * *

UNITED STATES PATENT AND TRADEMARK OFFICE
CERTIFICATE OF CORRECTION

PATENT NO. : 7,344,554 B2 Page 1 of 1
APPLICATION NO. : 10/375800
DATED : March 18, 2008
INVENTOR(S) : Charles C. Kuyava et al.

It is certified that error appears in the above-identified patent and that said Letters Patent is hereby corrected as shown below:

Column 6, line 3, start a new paragraph with "One example of a Keith needle ...".
Column 7, line 31, append the beginning of the paragraph to the end of the preceding paragraph.
Column 9, line 34, replace "wherein Keith needle" with --wherein the Keith needle--; line 35, replace "bare" with --bore--.
Column 11, line 22, replace "force3" with --force--; line 23, replace "pardon" with --portion--.
Column 12, line 30, insert the following claim: --30. The kit of Claim 22, wherein: the barrel bore has a bore axis extending between the barrel forward end and the tool handle; and the applying means comprises means for substantially aligning the needle shaft axis with the barrel bore axis minimizing contact of the needle shaft with the bore side.--
Column 12, line 31, replace "30" with --31-- and replace "28" with --30--; line 34, replace "shall" with --shaft--.

Signed and Sealed this

Twentieth Day of July, 2010

David J. Kappos
*Director of the United States Patent and Trademark Office*